(12) United States Patent
Kirstgen et al.

(10) Patent No.: US 11,648,051 B2
(45) Date of Patent: May 16, 2023

(54) SURGICAL INSTRUMENT (71) Applicant: Erbe Elektromedizin GmbH, Tuebingen (DE)

(72) Inventors: Udo Kirstgen, Rottenburg (DE); Volker Buntrock, Reutlingen (DE); Marcus Amann, Balingen Engstlatt (DE)

(73) Assignee: ERBE ELEKTROMEDIZIN GMBH, Tuebingen (DE)

(*) Notice: Subject to any disclaimer, the term of this patent is extended or adjusted under 35 U.S.C. 154(b) by 907 days.

(21) Appl. No.: 16/431,453

(22) Filed: Jun. 4, 2019

(65) Prior Publication Data
US 2019/0365459 A1 Dec. 5, 2019

(30) Foreign Application Priority Data

Jun. 5, 2018 (EP) .................................... 18176003

(51) Int. Cl.
*A61B 18/14* (2006.01)
*A61B 17/29* (2006.01)
*A61B 18/00* (2006.01)

(52) U.S. Cl.
CPC ...... *A61B 18/1447* (2013.01); *A61B 18/1445* (2013.01); *A61B 2017/2936* (2013.01);
(Continued)

(58) Field of Classification Search
CPC ...... A61B 18/1447; A61B 2018/00107; A61B 2018/00172; A61B 2018/00178;
(Continued)

(56) References Cited

U.S. PATENT DOCUMENTS 3,648,562 A * 3/1972 Loeble .................... F41A 19/13
89/185
4,033,043 A * 7/1977 Cunningham ......... A61B 17/88
33/542
(Continued)

FOREIGN PATENT DOCUMENTS

CN 203736304 U 7/2014
DE 102016106397 A1 10/2017
(Continued)

OTHER PUBLICATIONS

European Search Report dated Dec. 5, 2018, in corresponding European Application No. 18176003.4 (7 pages).
(Continued)

*Primary Examiner* — Joanne M Rodden
*Assistant Examiner* — Sean W Collins
(74) *Attorney, Agent, or Firm* — Fitch, Even, Tabin & Flannery LLP (57) ABSTRACT

A surgical instrument includes a jaw tool with two branches that can be closed for grasping tissue. In order to transmit the closing force to at least one branch, the branch is coupled with a preferably manually actuatable pull/push element, and, for coupling, an actuating pin that supports a sleeve interacts via the sleeve with a coupling track, in which case the sleeve rolls off the coupling track. In this manner, any deformation, abrasion or burr formation on the coupling track is prevented to such an extent that, even after numerous closing movements of the branches, the branches can still be actuated unimpaired by any wear of the coupling track and the actuating pin, respectively.

11 Claims, 7 Drawing Sheets

(52) U.S. Cl.
CPC .............. *A61B 2018/00107* (2013.01); *A61B 2018/00172* (2013.01); *A61B 2018/00178* (2013.01); *A61B 2018/00202* (2013.01); *A61B 2018/00589* (2013.01); *A61B 2018/00607* (2013.01); *A61B 2018/1452* (2013.01); *A61B 2018/1455* (2013.01)

(58) Field of Classification Search
CPC ........... A61B 2018/00202; A61B 2018/00589; A61B 2018/00607; A61B 2018/1452; A61B 2017/00845; A61B 2017/2936; A61B 2018/00083; A61B 2018/0063; A61B 2018/1455; A61B 18/1445; A61B 17/29; A61B 17/2909; A61B 17/295; A61B 17/32; A61B 18/12; A61B 2018/00428; A61B 2018/00601; A61B 18/1482; A61B 2018/126
See application file for complete search history.

(56) References Cited

U.S. PATENT DOCUMENTS

| | | | | |
|---|---|---|---|---|
| 4,444,365 A * | 4/1984 | Heuberger | ............... | B64C 39/12 403/DIG. 7 |
| 4,549,740 A * | 10/1985 | Nutter | ................. | F16D 3/841 277/637 |
| 5,391,180 A * | 2/1995 | Tovey | ............... | A61B 18/1445 606/174 |
| 5,403,342 A * | 4/1995 | Tovey | ................ | A61B 17/29 606/205 |
| 5,456,684 A * | 10/1995 | Schmidt | ................ | A61B 17/29 606/174 |
| 5,478,003 A * | 12/1995 | Green | ............. | A61B 17/07207 227/176.1 |
| 5,478,347 A * | 12/1995 | Aranyi | .................. | A61B 17/29 606/174 |
| 5,478,351 A * | 12/1995 | Meade | ................ | A61B 17/2909 606/174 |
| 5,490,819 A * | 2/1996 | Nicholas | .................. | A61B 1/32 606/205 |
| 5,496,317 A * | 3/1996 | Goble | ................ | A61B 18/1445 600/564 |
| 5,496,347 A * | 3/1996 | Hashiguchi | ............ | A61B 17/29 606/174 |
| 5,499,992 A * | 3/1996 | Meade | ................... | A61B 17/29 606/174 |
| 5,611,813 A * | 3/1997 | Lichtman | ........... | A61B 18/1445 606/174 |
| 5,620,458 A * | 4/1997 | Green | ............ | A61B 17/320016 604/104 |
| 5,674,230 A * | 10/1997 | Tovey | ................ | A61B 17/0469 606/139 |
| 5,755,732 A * | 5/1998 | Green | ............ | A61B 17/320016 30/2 |
| 5,849,022 A * | 12/1998 | Sakashita | ............... | A61B 17/29 606/174 |
| 6,171,195 B1 * | 1/2001 | Ferguson | ................ | F16D 1/033 411/513 |
| 6,405,424 B1 * | 6/2002 | Ferguson | ................ | B25B 27/16 411/513 |
| 6,458,130 B1 * | 10/2002 | Frazier | ............... | A61B 18/1445 606/208 |
| 6,511,480 B1 * | 1/2003 | Tetzlaff | ............. | A61B 18/1445 606/41 |
| 6,585,735 B1 * | 7/2003 | Frazier | ............... | A61B 18/1445 606/208 |
| 7,131,971 B2 * | 11/2006 | Dycus | ................ | A61B 18/1445 606/49 |
| 8,632,539 B2 * | 1/2014 | Twomey | ............ | A61B 18/1445 606/51 |
| 8,968,311 B2 | 3/2015 | Allen, IV et al. | | |
| 9,107,672 B2 * | 8/2015 | Tetzlaff | ............. | A61B 18/1445 |
| 9,113,903 B2 * | 8/2015 | Unger | ................. | A61B 18/1445 |
| 9,439,666 B2 * | 9/2016 | Kerr | ................. | A61B 18/1206 |
| 9,480,522 B2 * | 11/2016 | Horner | ............... | A61B 17/295 |
| 9,549,775 B2 * | 1/2017 | Dumbauld | ......... | A61B 18/1445 |
| 9,877,776 B2 * | 1/2018 | Boudreaux | ........ | A61B 18/1447 |
| 9,918,782 B2 * | 3/2018 | Unger | ................. | A61B 18/1445 |
| 10,172,668 B2 * | 1/2019 | Tetzlaff | ............. | A61B 18/1445 |
| 10,617,416 B2 * | 4/2020 | Leimbach | ............. | G16H 40/63 |
| 10,639,094 B2 * | 5/2020 | Larson | .............. | A61B 18/1445 |
| 10,828,084 B2 * | 11/2020 | Krastins | ............. | A61B 18/1485 |
| 2003/0018331 A1 * | 1/2003 | Dycus | ................. | A61B 18/1445 606/51 |
| 2003/0065358 A1 * | 4/2003 | Frecker | .................. | A61B 17/29 606/205 |
| 2003/0176879 A1 * | 9/2003 | Anderson | .......... | A61B 17/1227 606/151 |
| 2003/0181910 A1 * | 9/2003 | Dycus | ................. | A61B 18/1445 606/51 |
| 2004/0044363 A1 * | 3/2004 | Fowler | ............... | A61B 17/1285 606/205 |
| 2004/0097911 A1 * | 5/2004 | Murakami | ..... | A61B 17/320092 606/27 |
| 2004/0243125 A1 * | 12/2004 | Dycus | ................. | A61B 18/1445 606/171 |
| 2006/0079889 A1 * | 4/2006 | Scott | ................... | A61B 18/1445 606/45 |
| 2006/0084973 A1 * | 4/2006 | Hushka | ............... | A61B 18/1445 606/42 |
| 2006/0184198 A1 * | 8/2006 | Bales | ..................... | A61B 17/29 606/205 |
| 2008/0308602 A1 * | 12/2008 | Timm | .............. | A61B 17/07207 227/176.1 |
| 2008/0319442 A1 * | 12/2008 | Unger | ................ | A61B 18/1445 606/48 |
| 2009/0012520 A1 * | 1/2009 | Hixson | .............. | A61B 18/1445 606/51 |
| 2009/0182327 A1 * | 7/2009 | Unger | ................ | A61B 18/1445 606/51 |
| 2010/0031977 A1 | 2/2010 | Sales | | |
| 2010/0036380 A1 * | 2/2010 | Taylor | .............. | A61B 17/00234 606/205 |
| 2010/0179545 A1 * | 7/2010 | Twomey | ............ | A61B 18/1445 606/51 |
| 2010/0331883 A1 * | 12/2010 | Schmitz | ............. | A61B 17/0218 606/279 |
| 2011/0054468 A1 * | 3/2011 | Dycus | ................ | A61B 18/1442 606/45 |
| 2012/0059409 A1 * | 3/2012 | Reschke | ............ | A61B 17/2833 606/208 |
| 2012/0100547 A1 | 4/2012 | Danker | | |
| 2012/0215266 A1 * | 8/2012 | Jones | ................ | A61B 17/7086 606/86 A |
| 2013/0066303 A1 | 3/2013 | Hart | | |
| 2014/0012290 A1 | 1/2014 | Cooper et al. | | |
| 2014/0025070 A1 * | 1/2014 | Kerr | ..................... | A61B 17/295 606/41 |
| 2014/0221986 A1 * | 8/2014 | Kappel | ................ | A61B 17/29 606/1 |
| 2014/0257285 A1 | 9/2014 | Moua | | |
| 2014/0277049 A1 * | 9/2014 | Rethy | ................ | A61B 18/1445 606/180 |
| 2015/0066022 A1 * | 3/2015 | Shelton, IV | ......... | A61B 18/082 606/41 |
| 2015/0073451 A1 | 3/2015 | Guba et al. | | |
| 2015/0073462 A1 | 3/2015 | Guba et al. | | |
| 2015/0082928 A1 * | 3/2015 | Kappus | ............... | A61B 17/2909 74/103 |
| 2015/0272606 A1 * | 10/2015 | Nobis | ................ | A61B 18/1445 606/170 |
| 2015/0320437 A1 * | 11/2015 | Worrell | .......... | A61B 17/320068 606/169 |
| 2016/0157929 A1 * | 6/2016 | Kerr | ....................... | A61B 17/29 606/208 |
| 2016/0338718 A1 * | 11/2016 | Allen, IV | ................ | A61B 17/26 |
| 2016/0338762 A1 * | 11/2016 | Krastins | ............. | A61B 90/03 |
| 2016/0338763 A1 * | 11/2016 | Allen, IV | ................ | A61B 17/29 |
| 2016/0338764 A1 * | 11/2016 | Krastins | ............. | A61B 17/29 |

(56) References Cited

U.S. PATENT DOCUMENTS

| | | | |
|---|---|---|---|
| 2017/0135746 A1* | 5/2017 | Tetzlaff | A61B 18/1442 |
| 2017/0196622 A1* | 7/2017 | Nagtegaal | A61B 17/29 |
| 2017/0224332 A1* | 8/2017 | Hunter | A61B 17/068 |
| 2017/0296212 A1* | 10/2017 | Ding | A61B 17/295 |
| 2017/0325878 A1* | 11/2017 | Messerly | A61B 18/1445 |
| 2019/0110806 A1 | 4/2019 | Benk | |
| 2019/0261991 A1* | 8/2019 | Beckman | A61B 17/105 |
| 2019/0388143 A1* | 12/2019 | Kerr | A61B 17/29 |

FOREIGN PATENT DOCUMENTS

| | | |
|---|---|---|
| EP | 2361316 A1 | 8/2011 |
| EP | 2574299 A2 | 4/2013 |
| EP | 2659848 A2 | 11/2013 |
| EP | 2845548 A1 | 3/2015 |
| EP | 2845550 A1 | 3/2015 |
| JP | H06285078 A | 10/1994 |
| JP | 06311985 A | 11/1994 |
| JP | 2007195982 A | 8/2007 |
| JP | 2013523212 A | 6/2013 |
| JP | 2015054243 A | 3/2015 |
| JP | 2016518171 A | 6/2016 |

OTHER PUBLICATIONS

Office Action dated Apr. 28, 2022, in corresponding Russian Application No. 2019116378 (20 pages).

Chinese Office Action dated Feb. 23, 2022, in corresponding Chinese Application No. 201910487051.4, with English translation (22 pages).

Japanese Office Action for application No. 2019-100626 dated Dec. 19, 2022.

* cited by examiner

SURGICAL INSTRUMENT

RELATED APPLICATION(S)

This application claims the benefit of European Patent Application No. 18176003.4, filed Jun. 5, 2018, the contents of which are incorporated herein by reference as if fully rewritten herein.

TECHNICAL FIELD

The invention relates to a surgical instrument.

BACKGROUND

Hereinafter, the term "distal" always describes the part of the instrument or the component remote from the user, and the term "proximal" describes the part of the instrument or the component directed toward the user.

Publication EP 2 845 550 A1 describes a surgical instrument for coagulating, sealing and severing biological tissue such as, for example, blood vessels. The instrument comprises two branches that can be closed via pull/push elements in the manner of a pivoting motion, in which case a knife is supported between the push/pull elements in such a manner that it can be slid in longitudinal direction.

From publication EP 2 574 299 A2 an instrument has been known, said instrument comprising one movable and one stationary branch for grasping and clamping tissue, as well as for coagulation by the introduction of electrical current. The movement of an actuating lever is transmitted to the tool via a rod assembly. The rod assembly extends through the shaft. The rod assembly is comprised of a drive rod having a U-shaped cross-section in profile and of a knife rod positioned therein.

Publication EP 2 361 316 A1 discloses a surgical instrument with a movable branch that can be moved toward another branch for grasping tissue. The instrument comprises a handle, as well as an actuating lever. The movement of the actuating lever is converted—via an actuating gear mechanism—into a movement that is transmitted to the tool by pull/push and sliding elements that extend through the shaft.

Publication U.S. Pat. No. 8,632,539 B2 discloses a surgical instrument comprising two branches and a knife with a slot wherein a pull/push rod is arranged, via which the branches can be actuated.

Publication US 2013/0066303 A1 describes an instrument with two branches and a knife, in which case the knife can be moved in longitudinal direction in channels of the branches.

Publication DE 10 2016 106 397 A1 describes a surgical instrument with branches that are supported in a shaft in which connecting links for guiding the proximal end sections of the branches are formed in order to move said branches from an opened into a closed position. Actuating pins are provided on the proximal end sections of the branches, said pins being in engagement with respectively one recess in a pull/pressure rod for closing the branches.

Publication US 2010/0031977 A1 discloses an instrument with two forceps levers, wherein two clamps are provided on one forceps lever, said clamps being disposed for holding the two forceps levers together.

Considering this prior art, it is the object of the invention to state an improved surgical instrument.

SUMMARY

This object is achieved with a surgical instrument described below:

The surgical instrument according to a first aspect of the invention comprises a tool (jaw tool) with a first branch and a second branch, at least one of said branches being supported so as to be pivotable. The branches may also be referred to as claws or jaw parts. The instrument comprises a shaft having a distal end where the first tool is held. A push/pull element of the surgical instrument according to the invention is coupled—via a coupling structure—with the at least one pivotally movably supported branch for closing the branches. For example, the pull/push element can extend through the shaft. Alternatively or additionally, the pull/push element may extend next to the shaft, for example, and/or the pull/push element may enclose the shaft, for example. The surgical instrument according to the invention is distinguished in that the coupling between the pull/push element and the pivotally movably supported branch has an actuating pin and a coupling track, in particular a sliding link track, and the actuating pin is in engagement with the coupling track via a sleeve for coupling the pivotally movably supported branch with the pull/push element, said sleeve being rotatably supported by the actuating pin.

Between the support of the coupling track and the support of the actuating pin, a force is transmitted from the pull/push element to the pivotally movably supported branch via the coupling track and the actuating pin. Preferably, the coupling track is a sliding link track that specifies the conversion of the translatory motion of the pull/push elements into the pivoting motion of the pivotally movably supported branch.

The sleeve that is rotatably supported by the actuating pin rolls off the coupling track and slides on the actuating pin. In preferred embodiments, the actuating pin and the coupling track forming a sliding link track are in engagement with each other via the sleeve rolling off the sliding link track, so that a pull/push movement of the pull/push element is converted into a closing or opening movement of the at least one branch. Opposite an instrument, wherein an actuating pin slides on a coupling track, in particular a sliding link track, without sleeve, so that the actuating pin is in sliding friction on the coupling track, there will be a rolling friction between the sleeve and the coupling track, in particular the sliding link track, and a sliding friction between the actuating pin and the sleeve in the instrument according to the invention. In the event of a specified coupling track, the contact surface between the actuating pin and the sleeve, via which contact surface the sliding friction occurs, may be larger due to the round shape of the sleeve than between an actuating pin having the outside diameter of the sleeve, which slides on the specified coupling track without sleeve while a sliding friction occurs between the actuating pin and the coupling track.

It has been found that the jaw tool of the surgical instrument according to the invention can still be actuated smoothly and without impairment caused by friction-induced wear—even after numerous closing movements of the at least one branch, for example 250 closing movements. In particular, re-shaping or abrasion on the actuating pin or the coupling track or sliding link track due to the sleeve can be prevented or minimized, which could impair controllability of the first tool. In particular a burr or notch formation on the coupling track or sliding link track is minimized Thus, the useful life of the jaw tool is increased. With the sleeve it is possible to decrease losses due to friction-caused wear and/or friction losses, so that also a high desired clamping force on the tip of the branches can be applied with still acceptable manual force. Sleeves of coated or not coated metal, in particular stainless steel, or ceramic, are preferred.

The sleeve that is supported by the actuating pin preferably has a bottom, in particular a closed bottom. Thus the sleeve can be fabricated with thin walls because the bottom increases the stability of the sleeve. In this manner, even thin-walled sleeves will not be subject to denting of the edge of the sleeve. Due to a cup-shaped sleeve that may have a closed bottom, the stability of even a thin-walled sleeve is noticeably increased, in particular on the edge.

Preferably, the actuating pin is conical, in particular conically tapering toward its free end. Preferably, the space delimited by the sleeve is also conical, in particular shaped like a conical section. If the sleeve has a bottom, the inside space of the sleeve preferably tapers conically toward the bottom. The outside form of the sleeve preferably has the form of a conical section or a cylinder.

An actuating pin that is cone-shaped or has the shape of a conical section can optimally interact with a sleeve that tapers conically on the inside, in particular if the sliding friction force is transmitted uniformly to the surface of the pin or the inside surface of the sleeve. Furthermore, there results an advantage during assembly of the surgical instrument. The part bearing the actuating pin, said part being the branch for example, may be a metal powder injection-molded part, for example. The latter can be released more easily from the injection mould when the actuating pin is conical. If the sleeve is also conical, it is possible due to the cup shape and with the bottom, respectively, to ensure that the sleeve is attached in the correct direction. Otherwise, there might even ensue increased abrasion or increased deformation of the actuating pin of the sleeve and/or the sliding link track.

Between the sleeve and the actuating pin there preferably is effective a coating of the sleeve and/or the actuating pin. For example, the coating may be arranged on the actuating pin, in particular only on the actuating pin. Together with the uncoated or coated sleeve and/or the coated or uncoated actuating pin, the coating forms a friction pair with a sliding friction that is lower than that between the base material of the sleeve and the base material of the actuating pin.

Between the actuating pin and the sliding link track, there preferably is effective not a solid, namely in particular a powdery, liquid or paste-like lubricant. Such a lubricant may be omitted, without impairment of the actuation of the first tool even after repeated use, when a sleeve as described hereinabove is rotatably supported by the actuating pin in order to roll off the sliding link track and transmit the force between the sliding link track and the actuating pin, and/or when the actuating pin and/or sliding link track are coated.

The surgical instrument may comprise another tool, in particular a knife or a water jet probe.

Preferably, the first branch as well as the second branch are supported so as to be pivotally movable.

In preferred embodiments, the distal end of the pull/push element is provided with a coupling element that has a first lateral wall and a second lateral wall that are located opposite each other. The lateral walls may have openings or may be closed. The lateral walls delimit a receiving space between the lateral walls. The receiving space may be a channel, a slot or a gap, for example. Preferably, the first lateral wall bears a first coupling structure, and the second lateral wall preferably bears a second coupling structure. The first coupling structure is in engagement with the first branch, and the second coupling structure on the opposite lateral wall is in engagement with the second branch. In the receiving space, there is arranged preferably another tool, in particular a knife, between the coupling structures in longitudinal direction of the shaft, or slidably guided between the coupling structures in longitudinal direction of the shaft. The coupling element comprises at least one connection of the two lateral walls in order to form a coupling body. For example, the coupling element may have a U-shaped cross-section, in which case the receiving space may be a slot between the two "legs" of the U-shape in order to guide the knife. The section of the receiving space that is taken up by the second tool, in particular the knife, between the outer limits of the second tool is preferably uninterrupted. Accordingly, the second tool, in particular the knife, does not require an oblong hole in the region in which the receiving space is guided. The second tool can be guided securely in the coupling element in the receiving space formed in the coupling element between the lateral walls or between the coupling structures.

In preferred embodiments the sliding link track is provided on the coupling element as the coupling structure, and the pivotally movably supported branch preferably has the actuating pin associated with the link guide. Alternatively, the sliding link track may be configured on the branch that is pivotally movably supported, and the actuating pin in engagement with the sliding link track may be configured on the coupling element.

The link guide, in particular a link guide arranged on the lateral wall of the coupling element may be formed, for example, by two opposing wall surfaces that delimit a recess, in particular a groove or a slot. Preferably, the recess has a bottom. The wall surfaces form the sliding link tracks for the conversion of the pulling movement or the pushing movement into a corresponding closing movement or opening movement of the branches. The actuating pin arranged on the branch or on the coupling element comes into engagement with the recess and preferably ends in the recess.

The sliding link track may be curved. Preferably, the sliding link track is inclined relative to the translatory movement direction or oriented inclined with respect to longitudinal direction of the shaft. Preferably, the sliding link track has sections that are oriented with different inclinations relative to the translatory movement direction or inclined relative to the longitudinal direction of the shaft. Preferably, the sliding link track has at least one bend. For example, opposite sliding link tracks or wall surfaces may have a bend so that they define a recess, in particular a groove, that have or describe a bend. In this manner, the transmission of movement by the pull/push element to the pivotable branch occurs successively during a progressing motion with two different conversions, in particular conversion steps, from the open position into the closed position of the branches.

The branch that is supported so as to be pivotally movable is preferably supported so as to be pivotally movable by means of a bearing pin on the shaft. For example, the bearing pin may be provided on the branch. The at least one branch is preferably pivotally supported in such a manner that the branch does not perform a translatory movement relative to the shaft during the pivoting movement.

In preferred embodiments, the first branch and the second branch are pivotally supported on the shaft, in which case the pivot axes of the branches are offset relative to each other.

Preferably a channel is arranged in or on the shaft in which channel the proximal end of the pivotally movably supported branch is guided, so that a movement of the proximal end of the pivotable branch in the direction transverse to a pivot plane—in which the proximal end of the pivotally movably supported branch is pivoted—is delimited or prevented.

Each of the first second branches of the surgical instrument according to the invention preferably has an electrical connection for connecting the first branch and the second branch to an RF generator. Preferably, an RF power may be applied to the first branch and the second branch in order to form a bipolar instrument for thermofusion.

Combinations of one or more of the features described hereinabove with the embodiments described hereinabove form additional preferred embodiments. Additional advantageous features and embodiments of the surgical instrument according to the first aspect can be learned from the dependent claims, as well as from the description hereinafter, and the figures of the drawings.

According to a second aspect of the invention, there is additionally stated a surgical instrument that is characterized in that the first branch and the second branch are supported in a pivotally movable manner, and a coupling element is provided on the distal end of the pull/push element, said coupling element having, on each opposite lateral walls of the coupling element, a coupling structure, of which one coupling structure is in engagement with one branch and the coupling structure on the opposite lateral wall is in engagement with the other branch, and the coupling element defines a receiving space between the lateral walls, in which receiving space an additional tool is arranged between the coupling structures in longitudinal direction of the shaft or is movably guided in longitudinal direction of the shaft. Referring to the surgical instrument according to the second aspect, in exemplary embodiments, there may be provided—between the pull/push element and the pivotally movably supported branches—a coupling by means of actuating pins, in which case a sleeve is rotatably supported by each of said pins. Exemplary embodiments of the surgical instrument according to the second aspect of the invention can be developed with any one or more of the features of the surgical instrument according to the invention of the present patent application.

BRIEF DESCRIPTION OF THE DRAWINGS

The drawings show in

DETAILED DESCRIPTION

Figure 1:
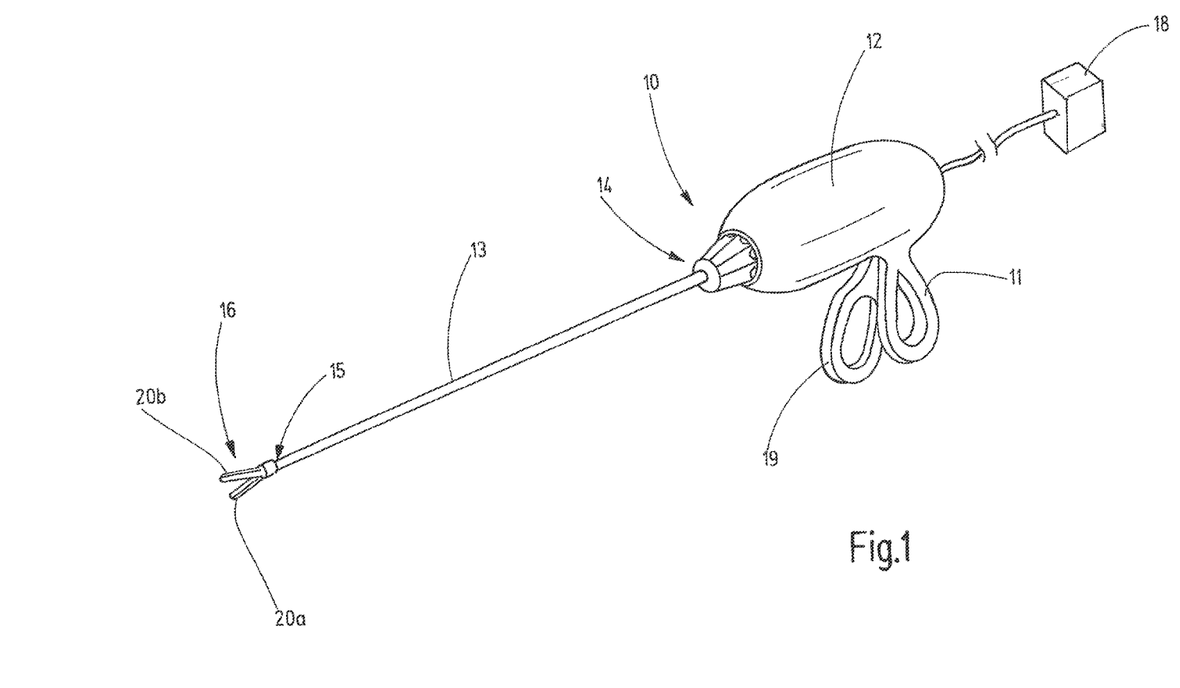
FIG. 1—a perspective schematic diagram of an embodiment of the surgical instrument according to the invention consistent with the first aspect and the second aspect of the invention, FIG. 2—a perspective representation of the first tool according to FIG. 1, FIG. 3—a perspective representation of a base part of the shaft belonging to the first tool according to FIG. 2, FIG. 4—a perspective representation of a branch of the first tool of the instrument according to the invention as in FIG. 2, with a sleeve for arrangement on the actuating pin of the branch, FIG. 5*a*—a perspective representation of a sleeve of the first tool of the instrument according to the invention as in FIGS. 1 and 2, FIG. 5*b*—a view of a longitudinal section through the center of the sleeve according to FIG. 5*a*, FIG. 5*c*—a detail of a longitudinal sectional view of the sleeve according to FIGS. 5*a*, 5*b* on the actuating pin of the branch as in FIG. 4, FIG. 6*a*—a pull/push element of the instrument according to the invention as in FIGS. 1 to 3, with a coupling element in which a knife is guided as an additional tool, FIG. 6*b*—a perspective view of the coupling element according to FIG. 6*a*, on the other side of the coupling element, and FIG. 7—an enlarged perspective view of a detail of the first tool according to FIG. 2.

FIG. 1 shows a surgical instrument 10 that comprises a housing 12 with a handle 11. The surgical instrument 10 has a shaft 13 whose proximal end 14 is held on the housing 12. The distal end 15 of the shaft 13 bears a first tool 16 to act on biological material, for example for clamping, coagulating and fusing. Extending through the shaft 13, there is a second tool 17, for example a knife 17, or a fluid line that is disposed for the subsequent severing of tissue, e.g., blood vessels. The surgical instrument 10 is preferably connected to an RF generator 18. Preferably, the surgical instrument 10 according to the invention is a bipolar instrument for thermofusion.

Figure 2:
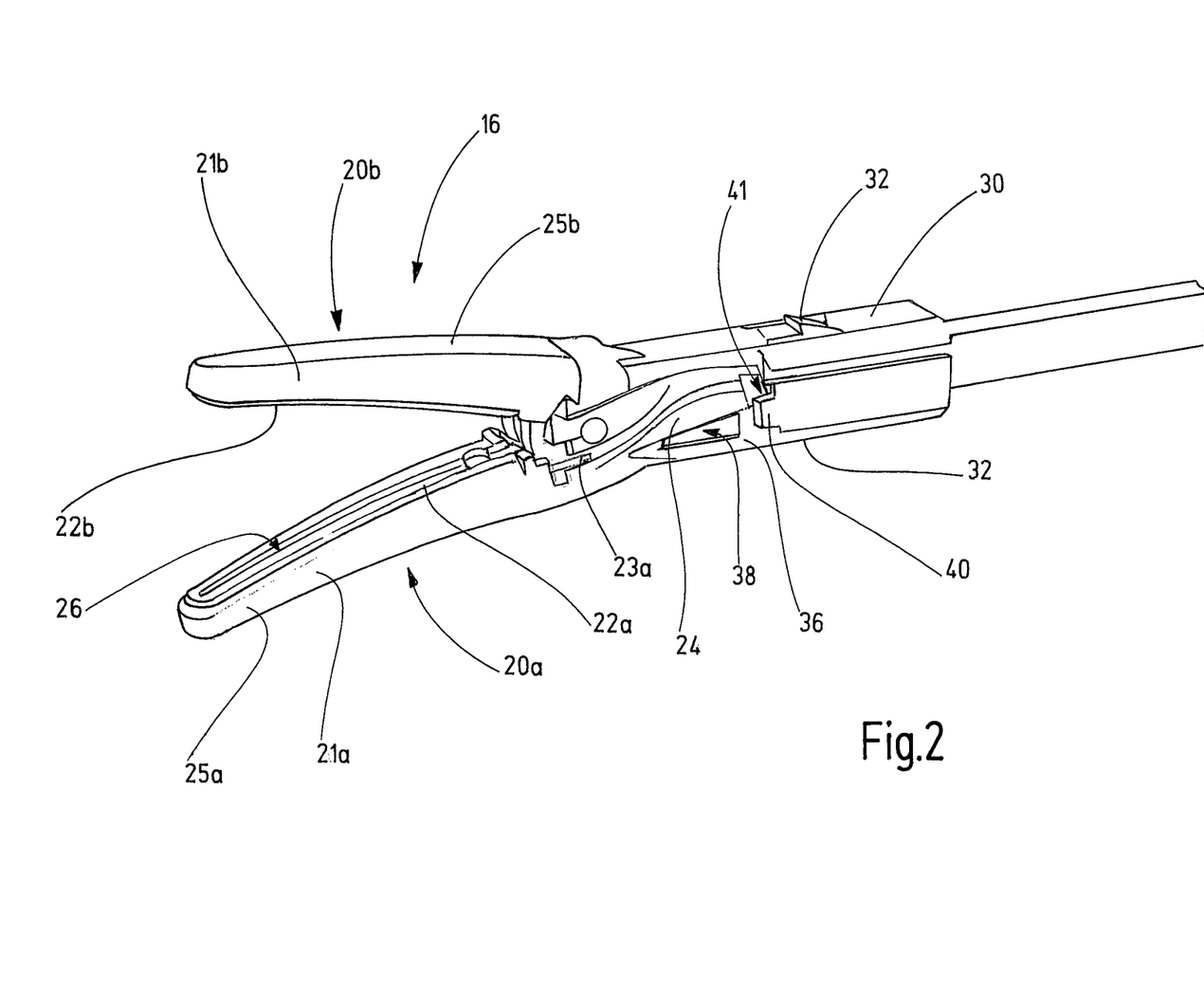

FIG. 2 shows the first tool 16 by itself. It comprises a first branch 20*a* and a second branch 20*b*, of which at least one—in the present exemplary embodiment both branches 20*a*, 20*b*—are supported so as to be pivotally movable about pivot axes. Each branch 20*a*, 20*b* consists of a branch support 21*a*, 21*b* and electrode units 22*a*, 22*b* fastened thereto. In doing so, the branch supports 21*a*, 21*b* are disposed for transmitting the mechanical forces and for supporting the branches 20*a*, 20*b*. Via connections 23*a*, the electrode units 22*a*, 22*b* are connected to electrical lines and, by way of this, the RF generator 18 can be charged with an electrical RF power. The electrical lines are not shown in the Figures to avoid confusion. In FIG. 2, the connection for the second branch 20*b* is concealed.

Figure 4:
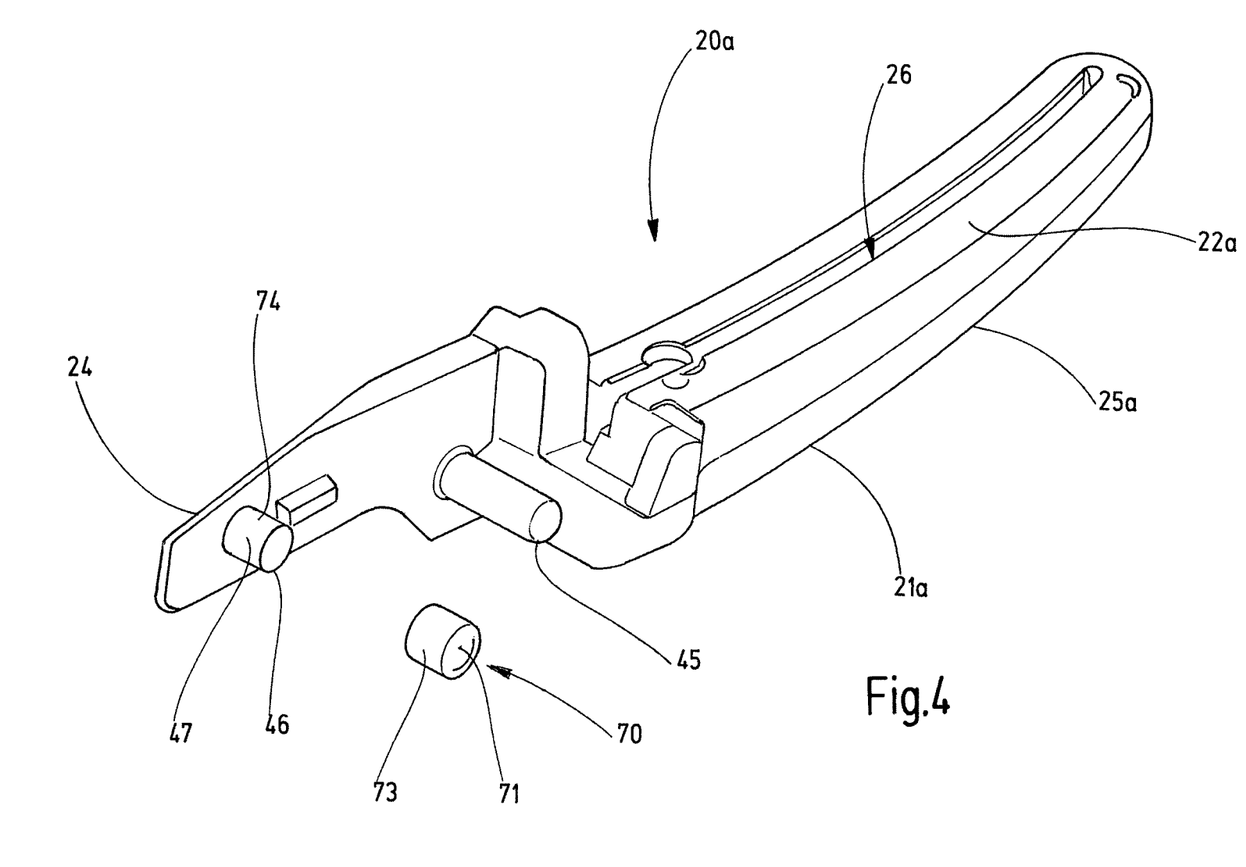

As can be seen in FIG. 4 in particular, explained here with reference to the first branch 20*a* as an example, in which case this is also applicable to the second branch 20*b*, the branch support 21*a* comprises an actuating section 24 and a support section 25*a*. The support section 25*a* supports the electrode unit 22*a*. Provided in the center of the electrode unit 22*a*, there is a channel 26 insulated on both sides or a knife guiding groove that is disposed to accommodate and guide a knife 17 (see, in particular, FIGS. 6*a*, 6*b*).

Figure 3:
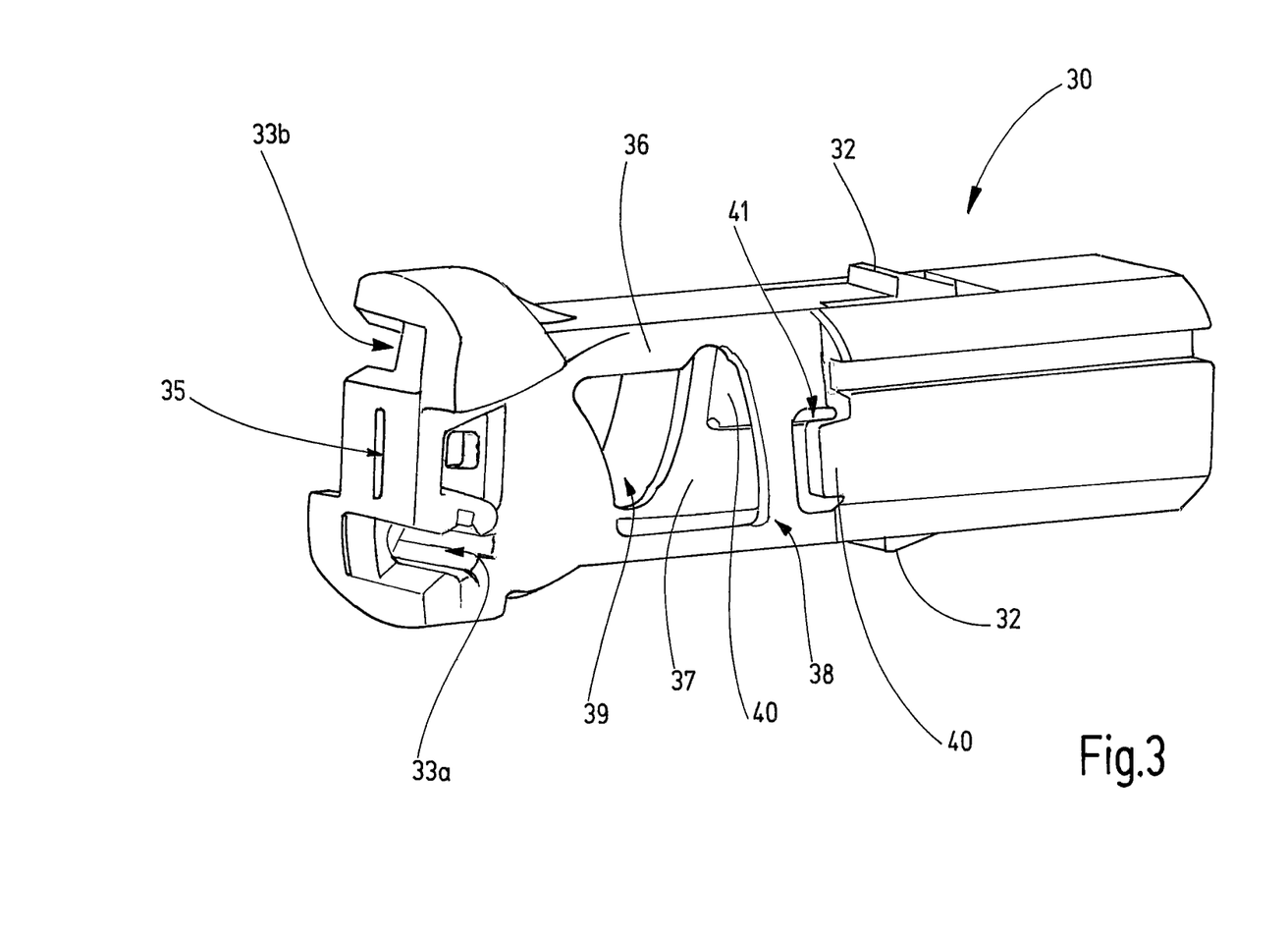

In the present exemplary embodiment, the shaft 13 has a distal section that is formed as the base part 30. It is shown separately in FIG. 3. The base part 30 may be made of plastic material, for example. The base part 30 may be connected to the remainder of the shaft extending up to the proximal end of the shaft 13 via a snap-lock connection. For this purpose, the illustrated base part 30 comprises locking catches 32. FIG. 2 does not show the remainder of the shaft 13. The branches 20*a*, 20*b* of the first tool 16 are pivotally supported by the base part 30. To do so, the base part 30 has bearing recesses 33*a*, 33*b*. The bearing recesses 33*a*, 33*b* are at a distance from each other such that the pivot axes do not coincide but are preferably parallel at a distance from each other. Thus, the second tool 17 can be guided between the bearing recesses 33*a*, 33*b* through the base part 30. In the present exemplary embodiment, the knife 17 is guided through the base part 30. To do so, a slot 35 is provided in the distal end of the base part in order to form a guide for the knife 17. The base part 30 has two opposing lateral walls 36, 37 that delimit a space between them. Each of the lateral walls 36, 37 has a window 38, 39, in which case the windows 38, 39 are located opposite each other. The base part 30 has two lateral extensions 40. Together with the lateral walls 36, 37, the extensions 40 form a channel 41, respectively.

The branches 20*a*, 20*b* (see, in particular, FIG. 4, using as example the first branch 20*a*) have, between the support section 24*a* and the actuating section 24, one bearing pin 45 each, said bearing pin being arranged in its associate bearing recess 33*a*, 33*b* in the base part 30 in order to support the branch 20*a*, 20*b* in a pivotally movable manner in the base part 30. As illustrated in FIG. 4 using as example the first branch 20*a*, there is arranged an actuating pin 46 on the actuating sections 24 of the branches 20*a*, 20*b*. The actuating pin 46 projects through the window 38 in the lateral wall 36 to the corresponding side of the base part 30. In the space delimited by the lateral walls 36, 37 of the base part 30, there extends—in longitudinal direction through the space—a pull/push element 50 having a coupling element 51 (coupling body) that is connected to a transmission section 52 of the pull/push element 50, in particular welded to or configured seamlessly in one piece with said transmission action. While the pull/push element 50 in the illustrated embodiment extends through the shaft 13, the pull/push element 50 in other embodiments of the instrument 10 according to the invention may extend parallel next to the shaft 13, for example, or it may be tubular and surround the shaft 13, for example.

Figure 6A:
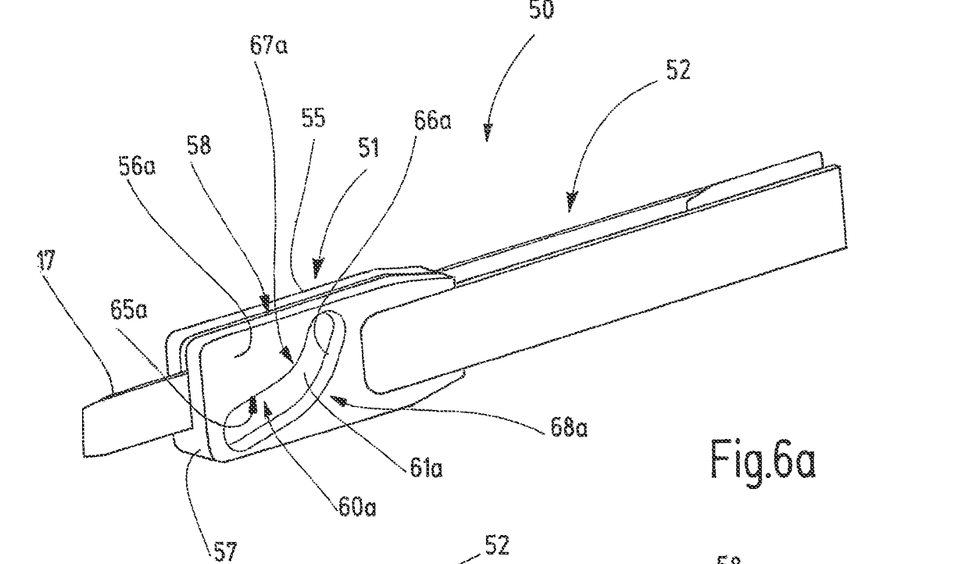
Figure 6B:
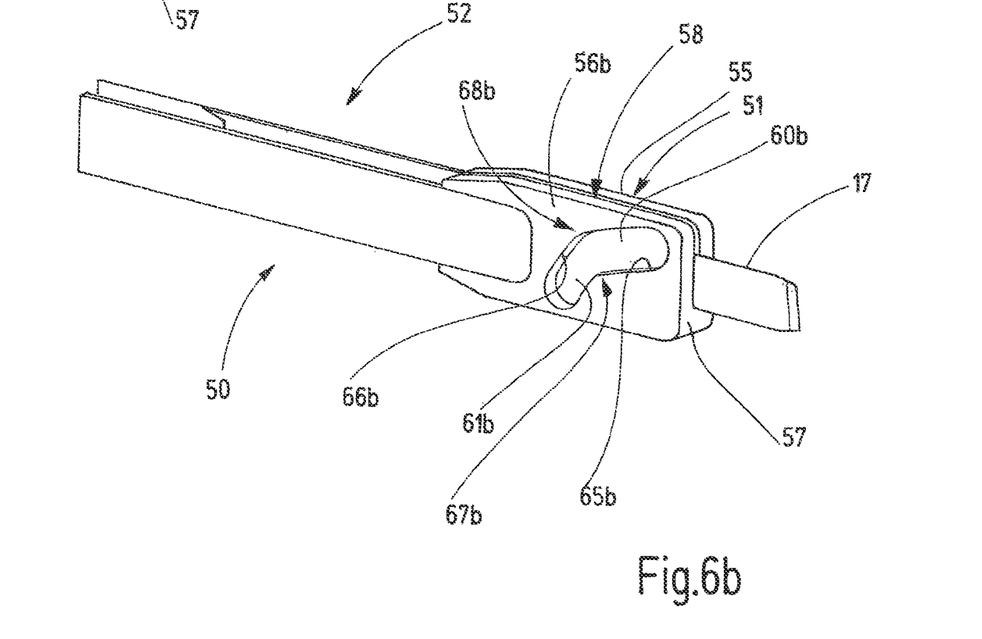

Preferably, the coupling element 51 is a metal part, in particular of stainless steel. The coupling element 51 consists of a body 55. The body 55 has two lateral walls 56*a*, 56*b* that are connected to each other via a bottom 57. In the slot-shaped receiving space 58 defined between the lateral walls 56*a*, 56*b*, the second tool 17—in the present exemplary embodiment a knife—is guided longitudinally. This is shown by FIGS. 6*a* and 6*b*. The FIGS. 6*a* and 6*b* are two perspective views of the coupling element 51, whose receiving space 58 a knife 17 is guided. The knife 17 extends through the receiving space 58 and into the transmission section 52.

Preferably, as in the illustrated exemplary embodiment, each lateral wall 56*a*, 56*b* has a groove 60*a*, 60*b*, of which—for reasons of illustration—FIG. 6*a* only shows the groove 60*a* in a lateral wall 56*a*. The actuating pin 46 of the first branch 20*a* engages in this groove 60*a*. FIG. 6*b* shows a coupling element 51 from the other side with the groove 60*b*, into which engages the actuating pin of the second branch 20*b*. The grooves 60*a*, 60*b* have a bottom 61, 61B, respectively. The receiving space 58 is arranged between the bottoms 61*a*, 61*b*. The grooves 60*a*, 60*b* are laterally delimited by two opposing wall surfaces that form sliding link tracks 65*a*, 65*b*, 66*a*, 66*b* of the sliding link guide that is configured in the form of the groove 60*a*, 60*b* on each lateral wall 56*a*, 56*b*. Instead of providing the sliding link tracks 65*a*, 65*b*, 66*a*, 66*b* on the coupling element 51 so that the coupling element 51 is the support (carrier) of the sliding link tracks 65*a*, 65*b*, 66*a*, 66*b*, and the actuating pins 46 are provided on the pivotally movable branch 20*a*, 20*b*, it is also possible—conversely—to arrange the sliding link tracks 65*a*, 65*b*, 66*a*, 66*b* on the branches 20*a*, 20*b* and the actuating pins 46 on the coupling element 51. The actuating pin 46 of the first branches 20*a* ends in the groove 60*a* on the first lateral wall 56*a*. The not illustrated actuating pin of the second branch 20*b* ends, accordingly, in the groove 60*b* of the second lateral wall 56*b*. The sliding link tracks 65*a*, 66*a* on the first lateral wall 56*a* interact with the actuating pin 46 of the first branch 20*a* in order to convert the translatory motion of the pull/push element 50 in longitudinal direction of the shaft 13 into a pivoting motion of the branch 20*a*. The same applies to the actuating pin of the second branch 20*b* and the associate sliding link tracks 65*b*, 66*b*.

The sliding link tracks 65*a*, 66*a* and 65*b*, 66*b*, respectively, have opposing bends (see reference signs 67*a* and 68*a* in FIG. 6*a*, as well as 67*b* and 68*b* in FIG. 6*b*) so that a groove 60*a*, 60*b* having a bend is formed, where the guiding direction changes abruptly before and after the bend, compared with a change of the guiding direction. The guiding direction specified by the sliding link tracks 65*a*, 66*a* and 65*b*, 66*b*, respectively, has on each section of the sliding link tracks 65*a*, 66*a* and 65*b*, 66*b*, respectively, a component with a direction opposite the pull/push direction. The bend results in a different conversion of the translatory motion of the pull/push element 50 into a pivoting motion of the branches 20*a*, 20*b*, before and after the actuating pin 46 is moved past the bend or past the bend on the actuating pin 46. The sections of the sliding link tracks before and after the bend may be straight or curved.

As illustrated by FIGS. 6*a* and 6*b*, the knife 17 is guided between the coupling structure having the sliding link tracks 65*a*, 66*a* on the first lateral wall 56*a* and the coupling structure having the sliding link tracks 65*b*, 66*b* on the second lateral wall 56*b* between the lateral walls 56*a*, 56*b*. The section of the receiving space 58 that is taken up by the knife between the outer edges of the knife 17 is not interrupted by a strip, for example, between the lateral walls 56*a*, 56*b*. As a result of this, the knife 17 need not necessarily have an elongated slot in the section of the knife 17 that is guided by the coupling element 51.

Figure 5A:
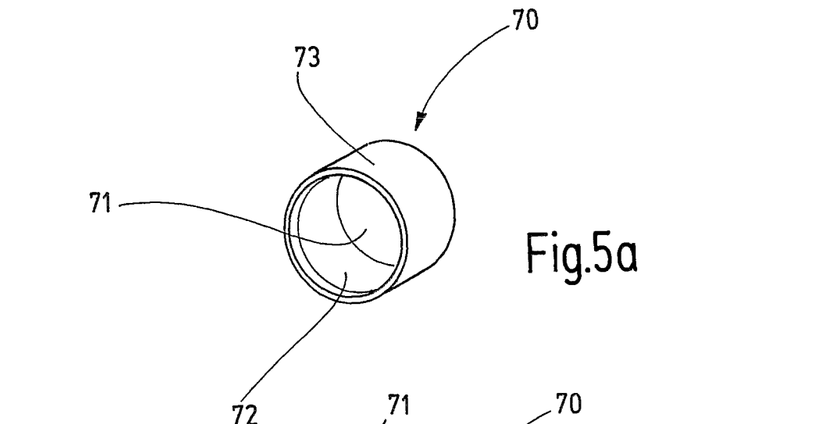
Figures 5B, 5C:
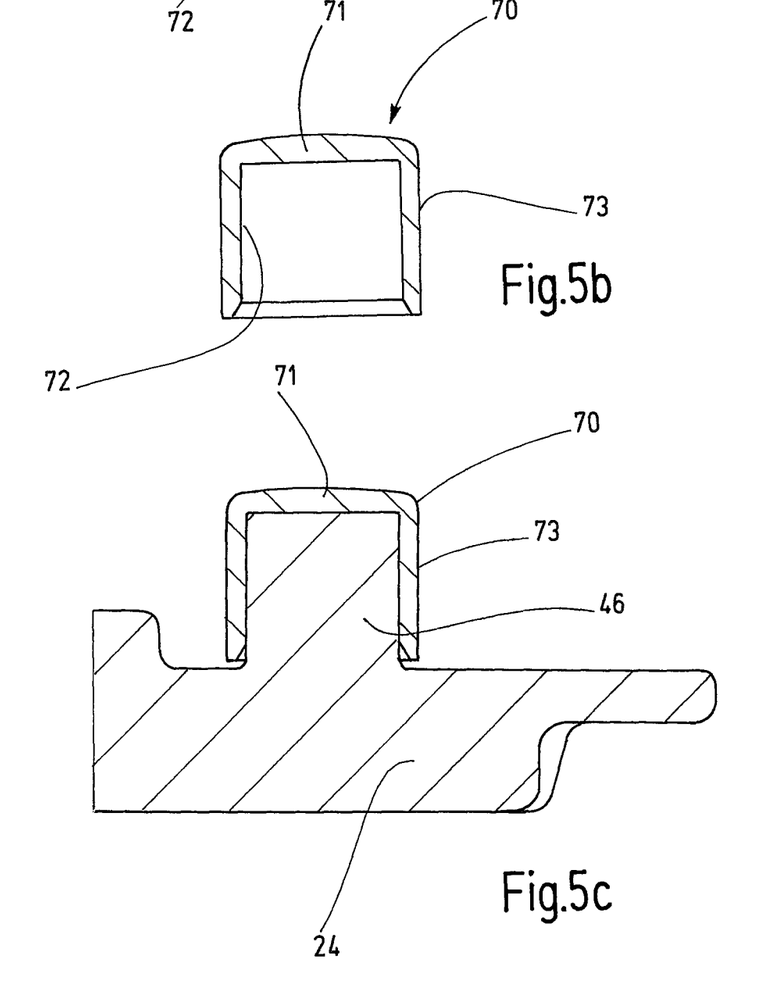

In FIG. 4 there is shown, in addition to the perspective representation of the first branch 20*a*, a sleeve 70 in perspective, said sleeve being arranged so as to be rotatably supported in the assembled first tool according to FIG. 2 on the actuating pin 46. As is also illustrated by FIGS. 5*a*, 5*b*, 5*c*, the sleeve 70 preferably has the shape of a cup with a bottom 71. The bottom 71, as in the illustrated embodiment, is preferably closed. Otherwise, the bottom 71 may consist for examples of spokes. The bottom 71 stabilizes the edge 72 of the sleeve on which the bottom 71 is located. The sleeve 70 can be made with the bottom 71 to have a thinner wall than without bottom 71. Furthermore, the bottom 71 represents a defined abutment for the actuating pin 46 in actuating pin longitudinal direction (see FIG. 5*c* that shows a sectional representation through the actuating section 24 through the actuating pin 46 and the attached sleeve 70). During a relative movement of the actuating pin 46 in the groove 60*a* of the coupling element 51, the sleeve 70 rolls off the sliding link track 65*a* or 65*b* corresponding to the translatory motion of the pull/push elements, said track being defined by the wall surface delimiting the groove 60*a*. In doing so, the sleeve 70 slides on the actuating pin 46. In order to ensure that the sleeve 70 will roll off on the sliding link track 65*a* or 65*b* and ensure that the sleeve 70 will slide on the actuating pin 46, the ratio of the outside diameter of the sleeve 70 to the inside diameter of the sleeve 70 is chosen accordingly. The bottoms 61*a*, 61*b* of the grooves 60*a*, 60*b* form a boundary for a movement of the sleeves 70 on the actuating pins 46 in longitudinal direction of the actuating pins 46.

The base body of the sleeve 70 is preferably metal, in particular stainless steel, or ceramic. Between the sleeve 70 and the actuating pin 46 there is preferably effective a coating 74 for reducing the sliding friction. Preferably, the actuating pin 46 is provided with a friction reducing coating 74. Alternatively or additionally, the inside circumferential surface 72 of the sleeve 70 may also be coated with a sliding friction-reducing coating. The sliding friction-reducing coating may, for example, be a metallic, organic or ceramic coating. For example, the coating may be a diamond-like carbon layer. Diamond-like carbon refers to a diamond-like amorphous carbon.

The outer surface 73 of the sleeve 70 is preferably cylindrical. The inside diameter of the sleeve may taper slightly conically in the section of the inside circumferential surface 72 that is in sliding friction with the section of the outside circumferential surface 47 of the actuating pin 46 toward the bottom 71 of the sleeve 70. Likewise, the actuating pin 46 may taper slightly conically in the section of the circumferential surface 47 that forms a friction pair with the inside circumferential surface 72 toward the free end of the actuating pin 46. The opening angles of the section of the inside circumferential surface 72 as defined by the conical forms of the actuating pin 46 and the inside of the sleeve 70 and the section of the circumferential surface 47 may be the same. An actuating pin 46 having the shape of a conical section can optimally interact with an internally conically tapering sleeve 70, in particular when the sliding friction force is uniformly transmitted to the circumferential surface 47 of the actuating pin 46 and the inside circumferential surface 72 of the sleeve 70, respectively. In addition, there results an advantage in the assembly of the surgical instrument 10. For example, in the case of the branches 20a, 20b, they each may be a metal powder-sprayed component. In the case of a conically shaped actuating pin 46 it may be released better by the injection mould. If the sleeve 70 is also shaped conically on the inside, it must be ensured—due to the cup shape or with the bottom 71, that the sleeve 70 is placed in the correct direction on the actuating pin 46 in order to avoid any increased abrasion or increased deformation of the actuating pin 46 of the sleeve 70 and/or the sliding link tracks 65a, 65b and 66a, 66b, respectively.

Figure 7:
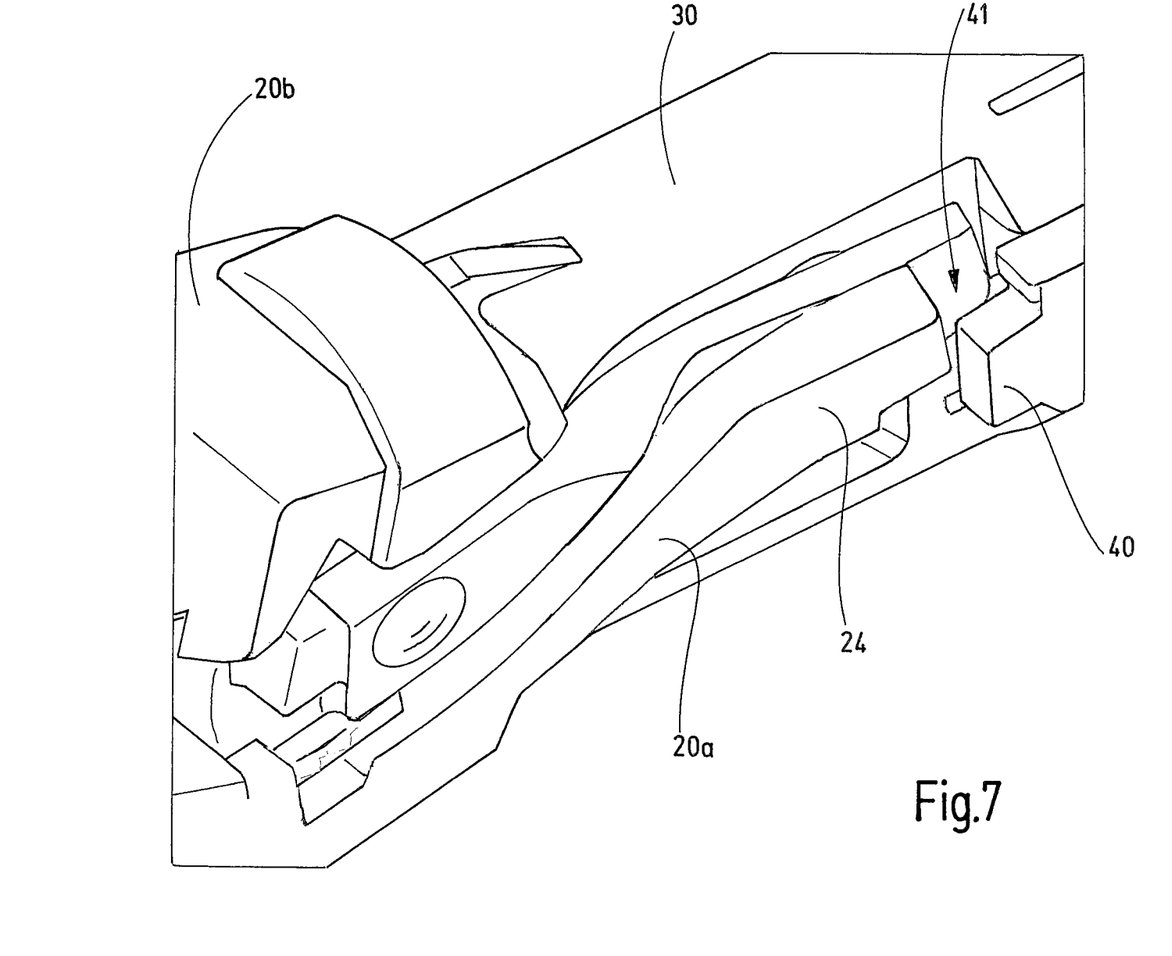

The proximal end of the actuating section 24 of the pivotally movably supported first branch 20a is preferably guided between the extension 40—that is supported by the base part 30 of the shaft 13—and the base part 30 in the channel 41. This is additionally illustrated by FIG. 7 that depicts an enlarged view of a detail of the first tool according to FIG. 2. As a result of this, a movement of the proximal end of the branch 20a in transverse direction with respect to the pivot plane away from the base part 30 is prevented or limited. This promotes the stability of the instrument 10 according to the invention.

The instrument 10 described so far operates as follows:

When not actuated, the branches 20a, 20b are spread away from each other and the knife 17 is in a retracted position. In this position, the pull/push element 50 can be biased by means of a compression spring (not illustrated) in distal direction, so that the branches 20a, 20b remain spread apart.

If the user now actuates the control lever 19 on the handle 11, this actuating movement is converted by a gear mechanism arranged in the housing 12 into a pulling movement that is transmitted to the proximal end of the pull/push element 50. This pulling movement in proximal direction closes the branches 20a, 20b, optionally against the force of the biasing element. When the branches 20a, 20b are being closed by retracting the pull/push element 50 in proximal direction, the actuating pin 46 is moved on the sliding link track 65a via the sleeve 70 rolling off the sliding link track, as a result of which the translatory movement of the pull/push element 50 is converted into a pivoting movement of the branch 20a. The same applies also to the second branch 20b.

Starting with fully opened branches 20a, 20b, they are closed when the pull/push element 50 is retracted at a constant speed with a first angular speed and, after the actuating pin 46 has moved through the region of the groove between the bent points, is closed at a second angular speed, wherein the second angular speed is lower than the first angular speed. After the bend has been moved past the actuating pin 46, however, the force transmission is greater than before. Due to the bend, the transmission of the translatory movement of the pull/push element 50 to the movably supported branches occurs in steps.

Preferably, the translatory motion of the coupling element 51 or the sliding link track effects a rotatory motion of the branches 20a, 20b within an angle of 0° to approximately 25°. In the exemplary embodiments, an actuating force on the control lever 19 of approximately 70 Newton can preferably achieve a clamping force of approximately 40 Newton on the distal end of the branches 20a, 20b.

With such a high clamping force on the jaw tool 16, there acts—caused by the one-sided force-injection into each branch 20a, 20b—a torque in opposite direction (asymmetrical force injection) on the branches 20a, 20b. Without the sleeves 70, high frictional forces would result in the coupling between the actuating pin 46 and the coupling element 51. However, the sleeves 70 can roll off on the sliding link tracks 65a, 65b, and thus less friction is generated. Thus the degree of efficacy between the manual force and the jaw tool clamping is increased and a long useful life of the tool 16 achieved.

The branches 20a, 20b grasp the biological tissue located between them and hold it clamped in place. By means of a not specifically illustrated switch and by activating a connected generator, a current may be applied via the electrode units 22a, 22b to tissue and a coagulation performed. If the coagulated tissue is now to be severed, for example, the knife 17 is moved in distal direction by a mechanism arranged in the housing. Said knife is guided securely in the coupling element 51 and the base part 30, even if the support sections 25a, 25b, as illustrated by FIGS. 2 and 4, are curved away from the pivot plane of the branches. Due to the guide, the knife 17 may not bend laterally outward but is securely guided in the knife guiding groove 26 and guided with the required force through denatured tissue in order to safely sever said tissue with a clean cut.

The surgical instrument 10 according to the invention comprises a jaw tool 16 with two branches 20a, 20b that can be closed for grasping tissue. In order to transmit the closing force to at least one branch 20a, 20b, the branch 20a, 20b is coupled with a preferably manually actuatable pull/push element 50, and, for coupling, an actuating pin 46 that supports a sleeve 70 interacts via the sleeve with a coupling track 65a, 65b; 66a, 66b, in which case the sleeve rolls off the coupling track 65a, 65b; 66a, 66b. In this manner, any deformation, abrasion or burr formation on the coupling track 65a, 65b; 66a, 66b is prevented to such an extent that, even after numerous closing movements of the branches 20a, 20b, said branches can still be actuated unimpaired by any wear of the coupling track 65a, 65b; 66a, 66b and the actuating pin 46, respectively.

LIST OF REFERENCE SIGNS

| | |
|---|---|
| 10 | Surgical Instrument |
| 11 | Handle |
| 12 | Housing |
| 13 | Shaft |
| 14 | Proximal end |
| 15 | Distal end |
| 16 | First tool |
| 17 | Second tool |
| 18 | RF generator |
| 19 | Control lever |
| 20a | First branch |
| 20b | Second branch |
| 21a | Branch support |
| 21b | Branch support |
| 22a | Electrode units |
| 22b | Electrode units |
| 23a | Connection |
| 24 | Actuating section |
| 25a | Support section |
| 25b | Support section |
| 26 | Channel/knife guide groove |
| 30 | Base part |
| 32 | Locking catches |
| 33a | Bearing recess |
| 33b | Bearing recess |
| 35 | Slot |
| 36 | Lateral wall |
| 37 | Lateral wall |
| 38 | Window |
| 39 | Window |
| 40 | Projection |
| 41 | Channel |
| 45 | Bearing pin |
| 46 | Actuating pin |
| 47 | Outside surface |
| 50 | Push/pull element |
| 51 | Coupling element |
| 52 | Transmission section |
| 55 | Body |
| 56a, 56b | Lateral walls |
| 57 | Bottom |
| 58 | Receiving space |
| 60a, 60b | Groove |
| 61a, 61b | Bottom |
| 65a, 65b | Sliding link track |
| 66a, 66b | Sliding link track |
| 67a, 67b | Bend |
| 68a, 68b | Bend |
| 70 | Sleeve |
| 71 | Bottom |
| 72 | Inner circumferential surface |
| 73 | Outer side surface |
| 74 | Coating |

The invention claimed is:

1. A surgical instrument (10) comprising:
a first tool (16) with a first branch (20a) and a second branch (20b), at least one of said first and second branches (20a, 20b) being a pivotally movably supported branch,
a shaft (13) having a distal end (15) on which the first tool (16) is held, and
a pull/push element (50) that is coupled via a coupling structure (46, 65a, 65b, 66a, 66b) with the at least one pivotally movably supported branch (20a, 20b) in order to close the first and second branches (20a, 20b),
wherein the coupling structure between the pull/push element (50) and the at least one pivotally movably supported branch (20a, 20b) comprises an actuating pin (46) and a coupling track (65a, 65b, 66a, 66b), the actuating pin (46) configured to couple the at least one pivotally movably supported branch with the pull/push element (50) and to be in engagement with the coupling track (65a, 65b, 66a, 66b) via a sleeve (70) that is rotatably supported by the actuating pin (46),
wherein the sleeve (70) is cup-shaped and includes a closed bottom (71) that extends over a free end of the actuating pin (46),
wherein the coupling track (65a, 65b; 66a, 66b) comprises first and second coupling tracks (65a, 65b; 66a, 66b), wherein the first branch (20a) and the second branch (20b) are supported so as to be pivotally movable, wherein on a distal end of the pull/push element (50) there is provided a coupling element (51) that has, on opposite lateral walls (56a, 56b) of the coupling element (51), the first and second coupling tracks (65a, 65b; 66a, 66b), wherein the first coupling track (65a, 66a) is in engagement with one of the first and second branches, and the second coupling track on the opposite lateral wall (56b) is in engagement with the other of the first and second branches, wherein the coupling element (51) defines, between the lateral walls, a receiving space (58) in which another tool (17) is arranged between the first and second coupling tracks (65a, 65b; 66a, 66b) or is guided in a sliding manner in a longitudinal direction of the shaft.

2. The surgical instrument (10) according to claim 1, wherein the actuating pin (46) tapers conically and wherein the sleeve (70) tapers conically on an inside of the sleeve.

3. The surgical instrument (10) according to claim 1, wherein, between the sleeve (70) and the actuating pin (46) there is a coating (74) of at least one of the sleeve (70) and the actuating pin (46).

4. The surgical instrument (10) according to claim 1, wherein at least one of the first and second coupling tracks (65a, 65b, 66a, 66b) comprises a sliding link track (65a, 65b; 66a, 66b), and between the sliding link track (65a, 65b; 66a, 66b) and the actuating pin (46) there is no solid, liquid or paste-like lubricant.

5. The surgical instrument (10) according to claim 1, wherein at least one of the first and second coupling tracks (65a, 65b, 66a, 66b) comprises a sliding link track (65a, 65b; 66a, 66b) and the sliding link track (65a, 65b; 66a, 66b) has at least one bend (67a, 67b; 68a, 68b), so that conversion of a translatory movement of the pull/push element (50) to a closing movement of the at least one pivotally movably supported branch (20a, 20b) takes place in two different conversion steps successively from a fully opened position of the at least one pivotally movably supported branch (20a, 20b) into a closed position of the at least one pivotally movably supported branch (20a, 20b).

6. The surgical instrument (10) according to claim 1, wherein at least one of the first and second coupling tracks (65a, 65b, 66a, 66b) comprises a sliding link track (65a, 65b; 66a, 66b) that includes a groove having a bottom (61a, 61b), wherein opposite wall surfaces delimit the groove.

7. The surgical instrument (10) according to claim 1, wherein at least one of the first and second coupling tracks (65a, 65b, 66a, 66b) comprises a sliding link track (65a, 65b; 66a, 66b) formed on the coupling element (51), and the actuating pin (46) is formed on one of the first and second branches (20a, 20b).

8. The surgical instrument (10) according to claim 1, wherein the first and second branches (20a, 20b) are each pivotally supported on the shaft (13) by a bearing pin (45).

9. The surgical instrument (10) according to claim 1, wherein pivot axes of the branches (20a, 20b) are offset relative to each other.

10. The surgical instrument (10) according to claim 1, wherein a proximal end of at least one of the first and second branches (20*a*, 20*b*) is guided in a channel (41) that is arranged in or on the shaft (13), so that a movement of the proximal end of the at least one of the first and second branches (20*a*, 20*b*) in a direction transverse to a pivot plane of the at least one first and second branches (20*a*, 20*b*) is limited or prevented.

11. The surgical instrument (10) according to claim 1, wherein the first branch (20*a*) and the second branch (20*b*) each has an electrical connection (23*a*) for connecting the first branch (20*a*) and the second branch (20*b*) to an RF generator (18).

* * * * *